(12) United States Patent
Chang et al.

(10) Patent No.: US 9,760,540 B2
(45) Date of Patent: Sep. 12, 2017

(54) METHODS FOR PROCESSING SEQUENTIAL DATA TO IDENTIFY POSSIBLE PEAK POINTS AND TO ESTIMATE PEAK TO NOISE RATIO OF SEQUENTIAL DATA

(71) Applicant: National Central University, Taoyuan County (TW)

(72) Inventors: Yi-Chung Chang, Taipei (TW); Men-Tzung Lo, Tainan (TW)

(73) Assignee: National Central University, Taoyuan (TW)

( * ) Notice: Subject to any disclaimer, the term of this patent is extended or adjusted under 35 U.S.C. 154(b) by 1135 days.

(21) Appl. No.: 13/682,757

(22) Filed: Nov. 21, 2012

(65) Prior Publication Data

US 2014/0142894 A1     May 22, 2014

(51) Int. Cl.
*G06F 17/18* (2006.01)
*A61B 5/0444* (2006.01)
*A61B 5/00* (2006.01)

(52) U.S. Cl.
CPC ............ *G06F 17/18* (2013.01); *A61B 5/0444* (2013.01); *A61B 5/4362* (2013.01)

(58) Field of Classification Search
CPC .................................................. A61B 5/0444
See application file for complete search history.

(56) References Cited

U.S. PATENT DOCUMENTS

| | | | |
|---|---|---|---|
| 3,984,772 A | 10/1976 | Bohler et al. | |
| 6,460,001 B1 | 10/2002 | Yamaguchi et al. | |
| 2009/0030616 A1 | 1/2009 | Sugiura | |
| 2010/0214590 A1 | 8/2010 | Ray et al. | |
| 2010/0274145 A1* | 10/2010 | Tupin, Jr. ............. | A61B 5/0444 600/511 |
| 2010/0303374 A1 | 12/2010 | Mizuno | |

FOREIGN PATENT DOCUMENTS

| | | |
|---|---|---|
| CN | 102098246 A | 6/2011 |
| CN | 101856225 B | 7/2011 |
| CN | 101828918 B | 9/2011 |
| CN | 102651636 A | 8/2012 |
| TW | 483636 U | 4/2002 |
| TW | 200809216 | 2/2008 |

OTHER PUBLICATIONS

Abraham Savitzky and Marcel J. E. Golay, Smoothing and Differentiation of Data by Simplified Least Squares Procedures (Analytical Chemistry, vol. 36, No. 8, Jul. 1964, pp. 1627-1639).*
Wikipedia Gaussian Blur (https://web.archive.org/web/20110921125716/http://en.wikipedia.org/wiki/Gaussian_blur retrieved by Archive.org on Sep. 21, 2011).*

* cited by examiner

*Primary Examiner* — Paul D Lee
*Assistant Examiner* — Mark Crohn
(74) *Attorney, Agent, or Firm* — CKC & Partners Co., Ltd.

(57) ABSTRACT

A method implemented through an electronic system for processing a sequential data to identify possible peak points is disclosed. The method defines a decayed threshold function and partition the sequential data into a plurality of segments by grouping each data point with surrounding data points into one of the segments. After that, a plurality of weighted segments are derived through weighting the surrounding data points by the decayed threshold function in each of the segments, and the peak points are identified through corresponding weighted segment.

4 Claims, 9 Drawing Sheets

METHODS FOR PROCESSING SEQUENTIAL DATA TO IDENTIFY POSSIBLE PEAK POINTS AND TO ESTIMATE PEAK TO NOISE RATIO OF SEQUENTIAL DATA

BACKGROUND

Field of Invention

The present invention relates to signal processing. More particularly, the present invention relates to periodic signal processing.

Description of Related Art

A number of nature signals are periodic or quasi-periodic signals, some of them come with other stronger signals that have some unpredictable noise or spikes on it, therefore, are not easy to identifiable them. Periodic signals are usually characterized by amplitude and frequency of it, and hence traditional ways to identify them by using some kinds of filters or particular procedures in time-frequency domain. However, these approaches need certain pre-know properties such as stationary of frequency and amplitude or assumption that signal are linear combined, and so on. But sometimes nature signals do have unpredictable properties such as non-stationary period or arbitrary morphology on it and hence are hard and even impossible to identify them from the mixtures of unpredictable noise or spikes. Obviously, there is no way to identify well on a total unpredictable signal, but away from that, periodic or quasi-periodic signals do have some properties that can be used to recognize them.

Identifying peaks or spikes of periodic signals is important, because they indicate significant events in many applications, such as heart contraction, sudden increase in price/volume, sharp rise in demand, bursts in data traffic, etc. The present disclosure identify peaks uses the nature of the periodic signal with two assumptions of it. One is that the signal or transformation of it should have one peak or maximal point within each cycle that peak to peak period is measurable, the other is these periods must have certain distribution rather than total random signals. It is hypothesized that the signal repeats a pattern as well as the peak over identical subsequent periods and hence the periodic statistical property can be measured through identifying peaks. Probability distribution is one of the periodic statistical properties used by present disclosure as a consequence to increase peak search accuracy from noise interfered signals and a basis to estimate the accuracy of such findings.

SUMMARY

A method, apparatus and system are provided that, in an embodiment, to identify peaks and improve the performance of identifying the periodic peaks by using the previously known probability properties.

According to one embodiment of the present disclosure, the method implemented through an electronic system for processing a periodic sequential data to identify possible peaks. This method requires defining a searching range for the local maximum and a decayed threshold function for peak detection. It partitions the original data into overlapping data segments by grouping each data point with surrounding points and the data points in each segment are multiplied by the decayed threshold function. As a result, the surrounding data points would be weighted while the center data point is not weighted and a peak point of a corresponding surrounding group is identified by checking that it is the largest data point in the group.

According to another embodiment of the present disclosure, in order to improve the accuracy of the next finding process recursively, the stochastic properties of past finding peaks are used to identify possible peaks and to correct possible mistakes. A probability weighting function is derived from stochastic properties of past finding peaks, and the original data is multiplied by it. The renewed peaks of the multiplied data are identified by passing through peak detection steps as mentioned before and the possible mistakes could be eliminated too. This recursive process is implemented to find the renewed peaks and to correct possible mistakes in the next finding process based on previous finding peaks repeatedly and could be stopped either in a particular number of times or on a certain situation.

According to still another embodiment of the present disclosure, a said probability weighting function is derived from past finding peaks. A probability weighting function is created according to the probability distribution derived from combining the scaled and replicated histograms copies of peak-to-peak intervals at each past finding peak location. This probability weighting function is then multiplied by original data to enhance the amplitude of probable peaks and suppress other signals. It means that the possible peaks could be identified and possible mistakes could be corrected.

According to still another embodiment of the present disclosure, the recursive interactions in the improvement of accuracy of the next finding process could be stopped on a certain situation that the improvements less than a certain extent. The improvement means the enhancement of the reliability of detected peaks. The reliability of detected peaks is according to the peak to noise ratio derived from the area average between two maximum curves of data. These two maximum curves are generated by the maximum values identified from divided segments of two groups of data which are sliding multiplied by different lengths of two decayed functions separately. The peak-to-noise ratio is calculated by averaging the area between two maximum curves. The larger peak-to-noise ratio refers to the higher correctness. If the improvement of peak-to-noise ratio is less than a certain extent, the recursive interactions in the improvement of accuracy of the next finding process will be stopped.

It is to be understood that both the foregoing general description and the following detailed description are by examples, and are intended to provide further explanation of the invention as claimed.

BRIEF DESCRIPTION OF THE DRAWINGS

The invention can be more fully understood by reading the following detailed description of the embodiment, with reference made to the accompanying drawings as follows.

DETAILED DESCRIPTION

Figure 1:
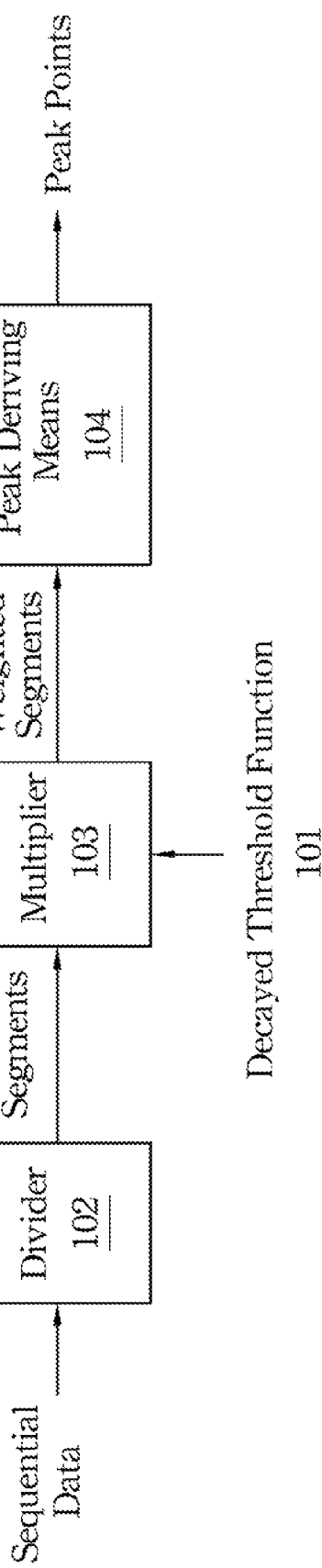
FIG. 1 shows a block diagram of a peak detector which detects peaks according to one embodiment of the present disclosure.

Reference will now be made in detail to the present embodiments of the invention, examples of which are illustrated in the accompanying drawings. Wherever possible, the same reference numbers are used in the drawings and the description to refer to the same or like parts.

As an embodiment, the algorithm of the present disclosure assume that periodic signals have been preliminary processed from blind source signals by a variety of signal processing methods such as signal subtracting at time domain that cancels out strong interference or uses Gabor transform ruling out the remnant signals of interference on frequency domain.

There are two assumptions of the present disclosure to identify peaks by using the nature of the periodic signal. One is that it should have one peak or maximum point within each cycle that peak to peak period is measurable, the other is these periods must have certain distribution rather than total random signals. Therefore, the peak-to-peak period is not random distributed in such kinds of signals, the most probable period can be derived from the histogram and likely range around a peak can thus be defined. For example, if the histogram of a period has a peak value at index N which means the peaks are likely to be happened every Nth point, hence, there is possibly a peak next to a peak within a range of 1.5N points and no chance to find another peak within the same range since it may needs 2N points. Such possible range (1.5N) can be thought as a "local" range as well as the peak itself can be thought as a local maximal point within that range.

To identify such local maximum points, the sliding window method with a proper size can be utilized. The advantage of this method is that it is not necessary to determine the threshold since the maxima is relative value. But since two maximum points cannot co-exist within one sliding window, a peak between two big peaks may not be detected if they get close enough. By adjusting the size of window to be smaller, such smaller peak can be detected as well as some unwanted spikes can be detected.

To tell the smaller peaks from unwanted spikes, this invention uses a weighted sliding window method to blurring the boundaries of range. Distance and amplitude are thus treated in more flexible way. The data points are suppressed with different ratio according to distance to the center, the greater distance to the center the more it has been suppressed. The maximal point occurs at center only when all suppressed points are smaller than the value at center, which means there is neither other larger points appear nearby the center nor much larger points far from the center. In other words, if the center point is a peak point, then the value of it must above the thresholds setting by any surrounding point. Thus, the middle area between two larger peaks will have higher sensitivity and lower threshold for peak detection than the other area between two peaks, a smaller peak in this area will get more chance to be detected. Conversely, unwanted spikes between two peaks may be excluded due to their smaller amplitude or irregular position that away from the middle area. The local maximum points thus become distance weighted maximum points with the consideration of both distance and amplitude and can be adjusted by different weighting function. Finally, connect maximum values of each segment of sliding window to form the maximum-curve and each local peak can be identified by checking that the center point is the largest value of the level-distant weighted data points of the segment. This is because that to find the maximum point of a segment equals to make comparisons with surrounding peaks on the distance decayed thresholds belonging to each surrounding peak.

Furthermore, peak identification can be vastly improved by utilizing probability weighting function derived from the histogram of peak-to-peak interval. It is because that the histogram of peak-to-peak interval surrounding of a peak is a kind of estimation of short range distribution. And the method extends the distribution to a larger range by scaling the histogram two or more times on time axis. As a result, a larger range distribution around a peak can be determined and a probability weighting function would be generated by the combination of all the larger range distribution at each occurrence time. By multiplying probability weighting function with the original data, this method creates a probability weighted data series.

The probability weighting function thus interfere the peak finding procedure by increasing the amplitude of probable points and suppressing unlikely ones according to the nearby probability distribution. And this method can further enhance the result by recursively finding peaks from the weighted data and updating the weighting function repeatedly. As weighting ratio also can be applied to the probability weighting function in case of over suppressing for outliers. The range of ratio may come from zero (no probability weighting) to one (full probability weighting) and may adjust according to the signal conditions and iteration number of time. For example, a noisier signal can use a light weighting factor during the first iteration because histogram may contain the noise. As the histogram contains fewer noises on the second iteration, it may increase the weighting factor.

Sometimes noise could be much greater than the periodic signal and hard to identify, peaks found by above steps will get mistakes. In order to estimate the reliability of each peak, a new parameter Peak-to-Noise Ratio (PNR) in an embodiment is developed. This method divides the sequential data into two groups of segments by using two different lengths of sliding windows, a large window and a smaller one. The shape of each sliding window is the same as previous one in peak detection step to follow that the center value is equal to a constant and decrease along each side Then, the data points inside window are multiplied by the two slide windows to generate two maximum-curve curves. As described previously, the curve with large window will ignore the small and irregular spikes between detected peaks and hence represents the amplitudes of detected peaks. On the other hand, curve with smaller window represents the amplitude of both detected peaks and the unwanted spikes since the window is small. Thus the area between two maximum-curve curves can be regarded as a kind of SNR for peaks, peak-to-noise ratio (PNR), that is, if unwanted spikes become larger, the two curves will get more dosed which lead to lower PNR value and vise versa.

To do a complete explanation, the fECG extraction hereinafter will be as examples to detail the each process of the algorithm according to the embodiments of the present disclosure.

Continuous Monitoring the baby's heart using fetal electrocardiogram (fECG) during pregnancy is important to present a risk to the fetus' safety. The fECG is derived from electrodes placed on the pregnant women's abdomen. Extracting the fECG signals from the composite maternal ECG signals obtained from abdominal leads is of great interest. The interfering maternal ECG signal is stronger than the fECG one; obviously, it is arduous to extract the fECG from abdominal signals recorded from abdomen electrodes. Since 1906, many different methods have been developed for detecting the fECG. One direct method subtracts a thoracic maternal ECG from the abdominal composite ECG. Direct subtraction techniques based on temporal or spatial filtering, subtraction of an averaged pattern and an adaptive impulse correlated filter. But, direct subtraction method suffers several limitations like placing a large number of electrodes in the same region, taking longer acquisition time, requiring many samples, and the accurate replica of the interference etc. Otherwise, many researches focused on fECG extraction by using blind source separation (BSS) and wavelet transform. Independent component analysis (ICA) is one of the BSS method applied to data recorded by electrocardiographic electrodes on the mother's abdomen. The limitations of ICA due to tissue conductivity, electrode efficiency, and other factors that may cause the signal mixture at the sensors to be non instantaneous. It also requires multiple leads for extraction of the fECG successfully. fECG separation in the wavelet domain introduces the permutation problem, which is a well known limitation of transform domain BSS, particularly for convolution mixtures, for which the separation matrix will be different in each subband, while in the case of instantaneous mixtures the mixing is in effect identical in each subband.

Applying the present disclosure on fECG extraction can rule out such limitations of other methods as mentioned above. The detail steps and explanations are described below.

Pre-Processing Using Garbor Transform

Seems the subtracted data may serious interfere by other noise that the waveforms are greatly distortion, peak detection from such data could be a problem. Through the time frequency analysis, the frequency bands of fECG, maternal ECG, EMG and thermal noise from skin could be known, hence these components can be separated from frequency domain by using Garbor transform.

On the other hand, the fECG wave morphology that follows the heart axis may vary over time, the waveform of QRS peaks could be upside-down due to different fetus position which may not be directly detected by finding maxima. By taking the amplitude of Garbor transform, the morphological information will transfer to the amplitude values in frequency domain that the local maximum method can be properly applied.

Although the fetal signal has been extracted and preprocessed initially, it is still intended to get occurring time of each peak in it. The further processing methods are emphasis on the present disclosure, described as the following:

Peaks Detection Using Distance Weighted Peak Detector

After the purified fECG is obtained, a window function with maximum value on the center that equal to one should be designed at first, it can regarded as a fading window, a Gaussian window with each side equal to 0.25 can be used for convenient. Next, the fading window is multiplied with the fECG data and the maximum value of these weighted points within the window would be found. Then, the next maximum value can be received by shifted the window to the next data point. By passing through all the subsequent data points, the maximum-curve curve is generated by connecting all the maximum values. At last, the peaks of the fECG would be decided by the equality test of original data and the maximum-curve curve.

FIG. 1 shows a block diagram of a peak detector which detects peaks according to one embodiment of the present disclosure. The peak detector which is implemented through an electronic system such as an electrocardiogram measure machine includes a divider 102, a multiplier 103, and a peak deriving means 104, and this peak detector is used for processing a psychological periodic signal, such as an electrocardiogram signal.

First, a decayed threshold function is defined, and the divider 102 partitions the sequential data into a plenty of segments by grouping each data point with surrounding data points into one of the segments, in which the sequential data is a two dimensional data, and the decayed threshold function is a two dimensional function. Next, the multiplier 103 derives a plenty of weighted segments through weighting the surrounding data points by the decayed threshold function in each of the segments. After that, the peak deriving means 104 identifies the peak points through corresponding weighted segment. In fact, the peak points are identified by checking if it has greatest amplitude comparing with surrounding data points within one of the weighted segments corresponding.

Probability Enhanced Peak Detection

In clinical, heart rate variability (HRV) is estimated through the variation of interval between the successive peak of ECG waves. Although the intervals vary between each beats, the heart rate unlikely to change dramatically in a short period of time (one to ten minutes for example). The heart beats are maintained by the autonomous nervous system and hence have some stationary property fulfilling the assumption of periodic signals. Through this property, a probability weighting function is designed to enhance the peak signals of fECG and suppress other ones.

Figure 2:
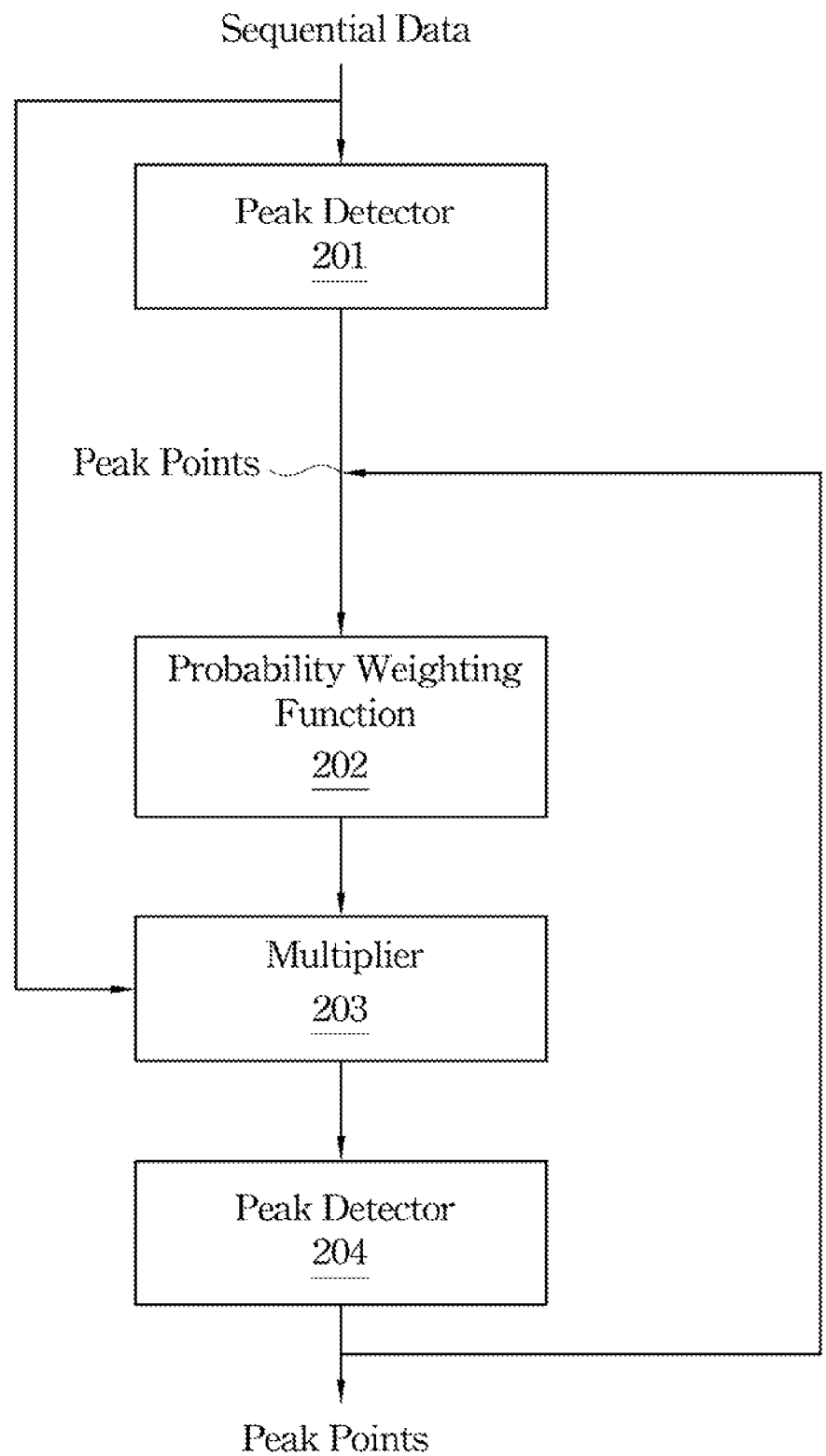
FIG. 2 is a flowchart of a method for processing sequential data to identify a plenty of possible peak points relating to stochastic properties of historical results according to one embodiment of the present disclosure.

FIG. 2 is a flowchart of a method for processing sequential data to identify a plenty of possible peak points relating to stochastic properties of historical results according to one embodiment of the present disclosure. A method, implemented through an electronic system, processes the sequential data to identify a plenty of possible peak points relating to stochastic properties of historical results. First, the possible peak points of the sequential data are identified through a peak detector in step 201, and a probability weighting function from the identified peak points are derived in step 202. Next, a weighted sequential data is derived through weighting the sequential data by the probability weighting function using a multiplier in step 203, and possible peak points of the weighted sequential data are identified in step 204. Step 202 to step 204 can be repeated to derive the peak points more accurately.

In more detail, step 201 and step 204 for deriving peak points define a decayed threshold function and partition the sequential data into a plenty of segments by grouping each data point with surrounding data points into one of the segments. Next, these steps derives a plenty of weighted segments through weighting the surrounding data points by the decayed threshold function in each of the segments and identifies the peak points through corresponding weighted segment.

Figure 3A:
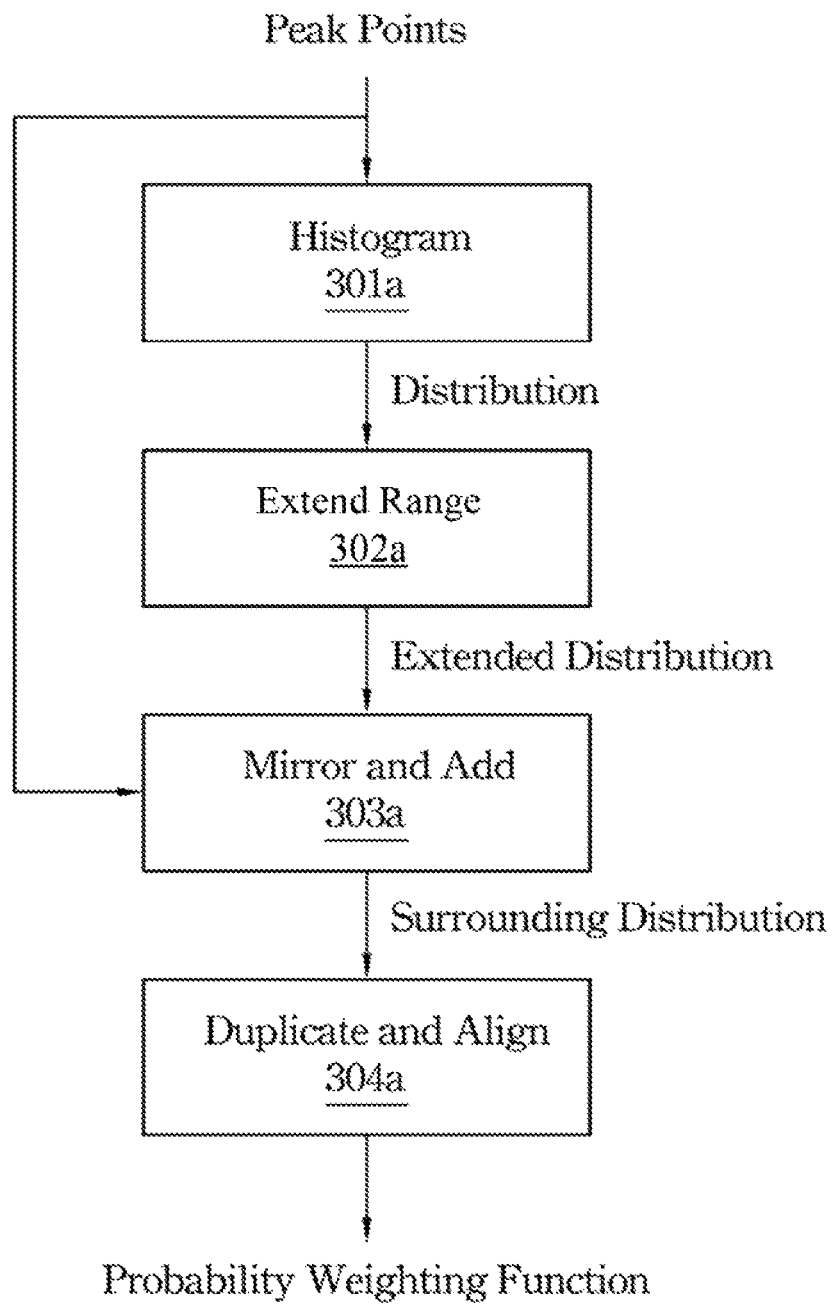
FIG. 3A is a flowchart of step for deriving the probability weighting function from the identified peak points according to one embodiment of the present invention.
Figure 3B:
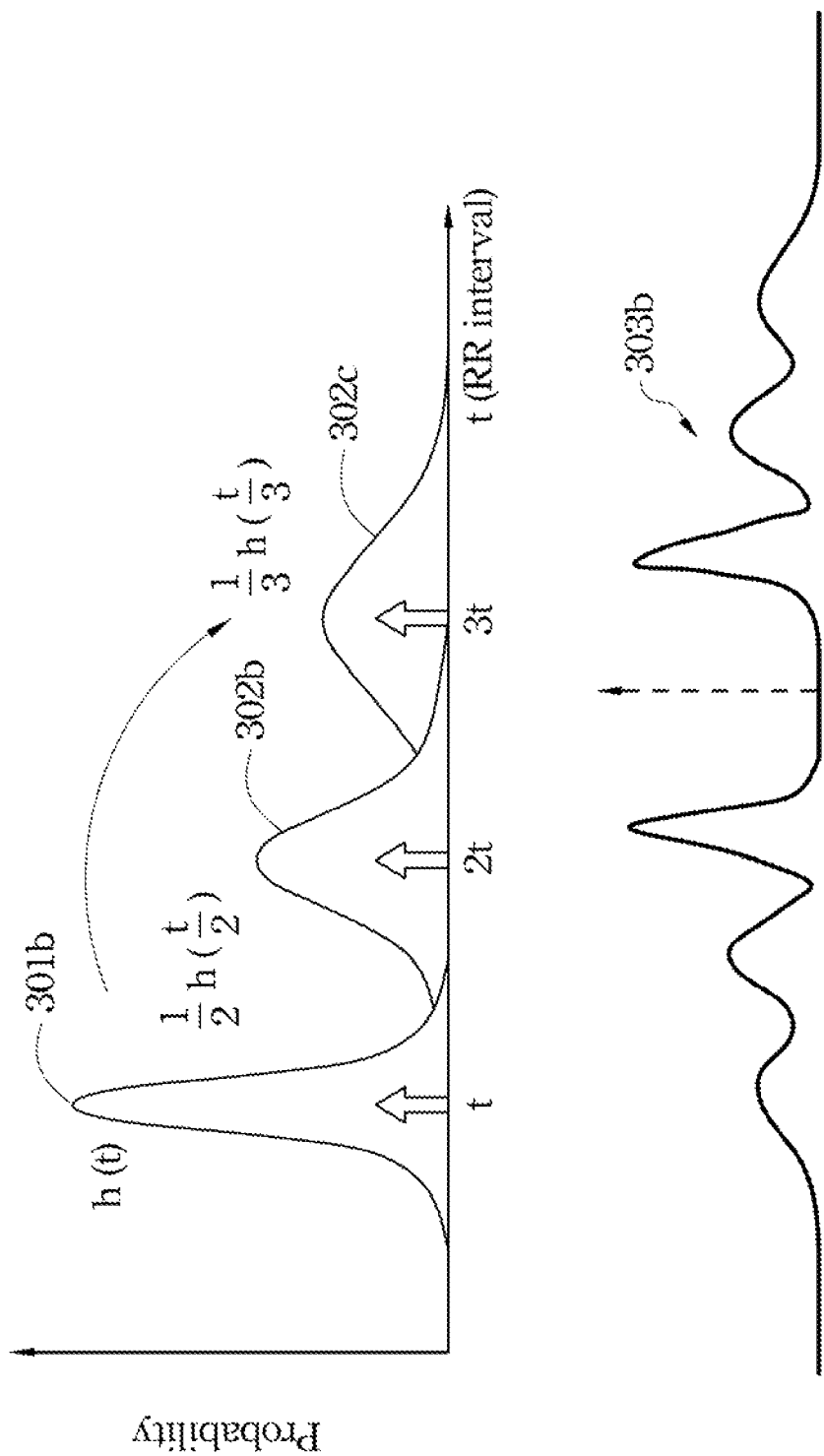
FIG. 3B is a diagram of a probability distribution and a two-side distribution of a weighting mask according to one embodiment of the present disclosure.
Figure 3C:
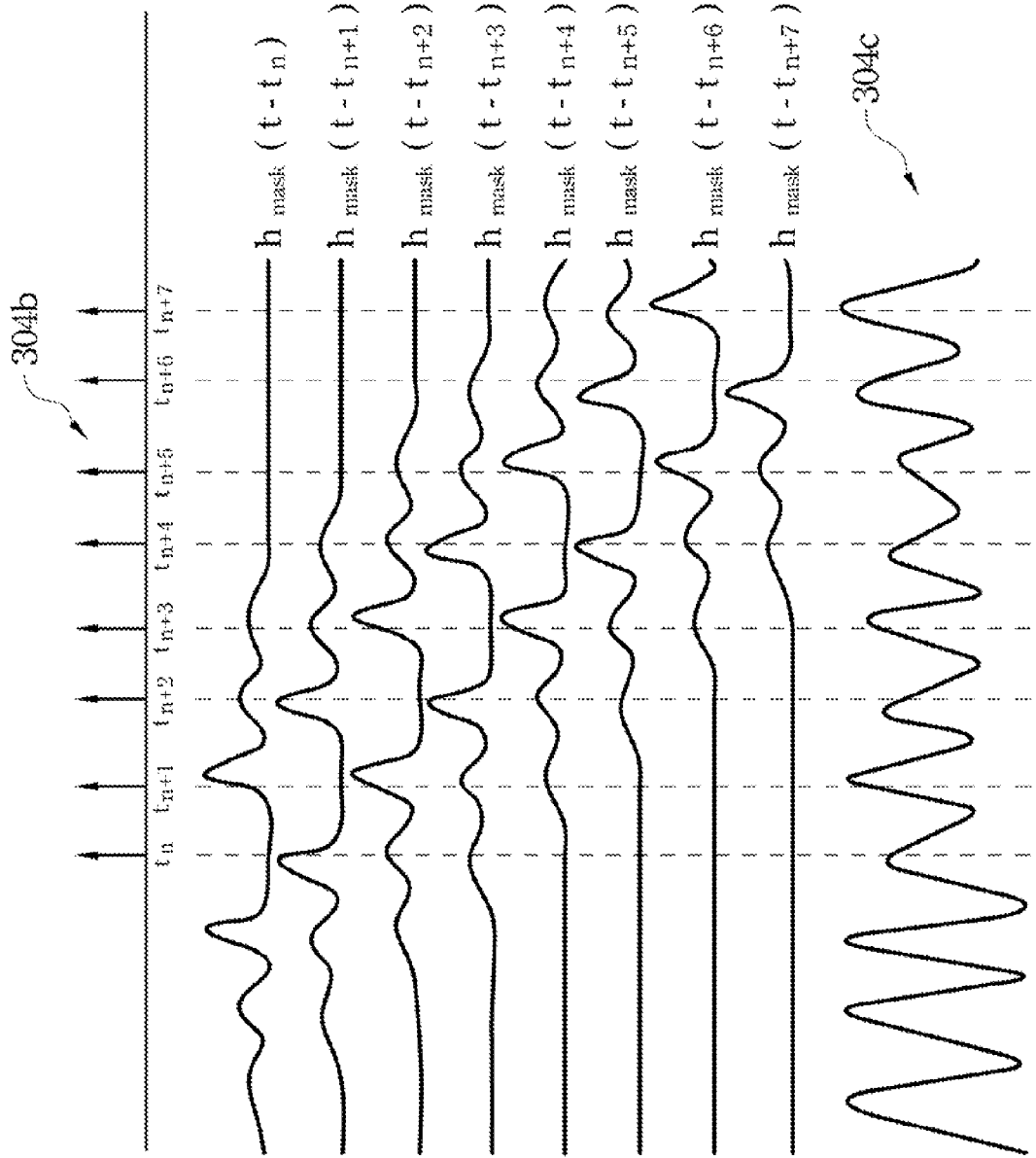
FIG. 3C is the schematic diagram of the weighting mask generating process according to one embodiment of the present disclosure.

FIG. 3A is a flowchart of step for deriving the probability weighting function from the identified peak points according to one embodiment of the present invention, FIG. 3B is a diagram of a probability distribution and a two-side distribution of a weighting mask according to one embodiment of the present disclosure, and FIG. 3C is the schematic diagram of the weighting mask generating process according to one embodiment of the present disclosure.

First, a distribution function is derived through creating and normalizing a histogram of a plenty of peak-to-peak intervals in step 301a. As shown in FIG. 3B, the time interval between the successive peaks of fECG signals can be obtained in the foregoing steps, the histogram hence can be plotted to show their probability distribution. This distribution (curve 301b) represents the short range distribution of peak occurring surrounding a peak.

The method provided by this invention extends the distribution to a larger range by scaling the histogram two (curve 302b) or more times on time axis, such as three times (curve 302c) on time axis. The method copies double and triple the size of the original histogram on time axis and apply proper weightings on them to normalize total probability. Then the two copies with half and one-third weightings are combined with the original histogram to be the one-side distribution on larger range, and the related formula is:

$$h_{d1}(t) = h(t) + \frac{1}{2}h\left(\frac{t}{2}\right) + \frac{1}{3}h\left(\frac{t}{3}\right).$$

An extended distribution is derived through adding different scale of copies of the distribution function together in step 302a.

Next, a surrounding distribution surrounding each peak point is derived through adding the extended distribution and a replicating of the extended distribution in opposite direction together in step 303a. After that, the distribution combined with its mirrored copy become the two-side distribution 303b of the weighting mask shown as FIG. 3B:

$$h_{d2}(t) = h_{d1}(|t|) = h(|t|) + \frac{1}{2}h\left(\frac{|t|}{2}\right) + \frac{1}{3}h\left(\frac{|t|}{3}\right)$$

The two-side distribution 303b is the probability distribution of occurring next peak according to each time to peak as the center.

After that, a plenty of copies of the surrounding distribution is duplicated in step 304a, and the centers of each copies are shifted to each identified peaks, and all the copies of the surrounding distribution are added together to form the probability weighting function in step 304a.

Finally, the probability weighting function 304c will be done by summing up the two-side distribution at times as shown in FIG. 3C. Weighting mask is then established by adding this probability weighting function of each peaks 304b according to each peak time, and the formula of weighting is represented as:

$$\text{mask}(t) = \sum_n h_2(t - t_n)$$

At last, the fECG signals are multiplied by the weighting mask and the peaks of the resulting signals are detected. As desired, the time interval between the successive peaks can be measured and the fetal HRV can be further explored too.

In more detail, a plenty of histograms are derived from different segments of identified peaks, and steps of deriving the probability weighting function further including defining a range for probability distribution estimation and dividing the identified peaks into segments according to the range; deriving histogram of peak-to-peak intervals of each segment and smoothing the histogram when the range is small; deriving the surrounding distribution for each histogram in each segments; and deriving the probability weighting function by choosing the closest surrounding distribution and shifting the centers of them to each identified peak and adding all of them together.

Since the histogram is always zero at the origin, the probability weighting function has zero value at the center. The input signal is multiplied by the weighting mask to become a probability weighted data series that will be enhanced by surrounding peaks if the interval between them is regular and will be suppressed if the interval is irregular. Next, apply the peaks detection method as mentioned previously to the weighted data series to find new peaks. By repeating such sequence two or three times can further enhance the peak detection of periodic signal.

Figure 4A:
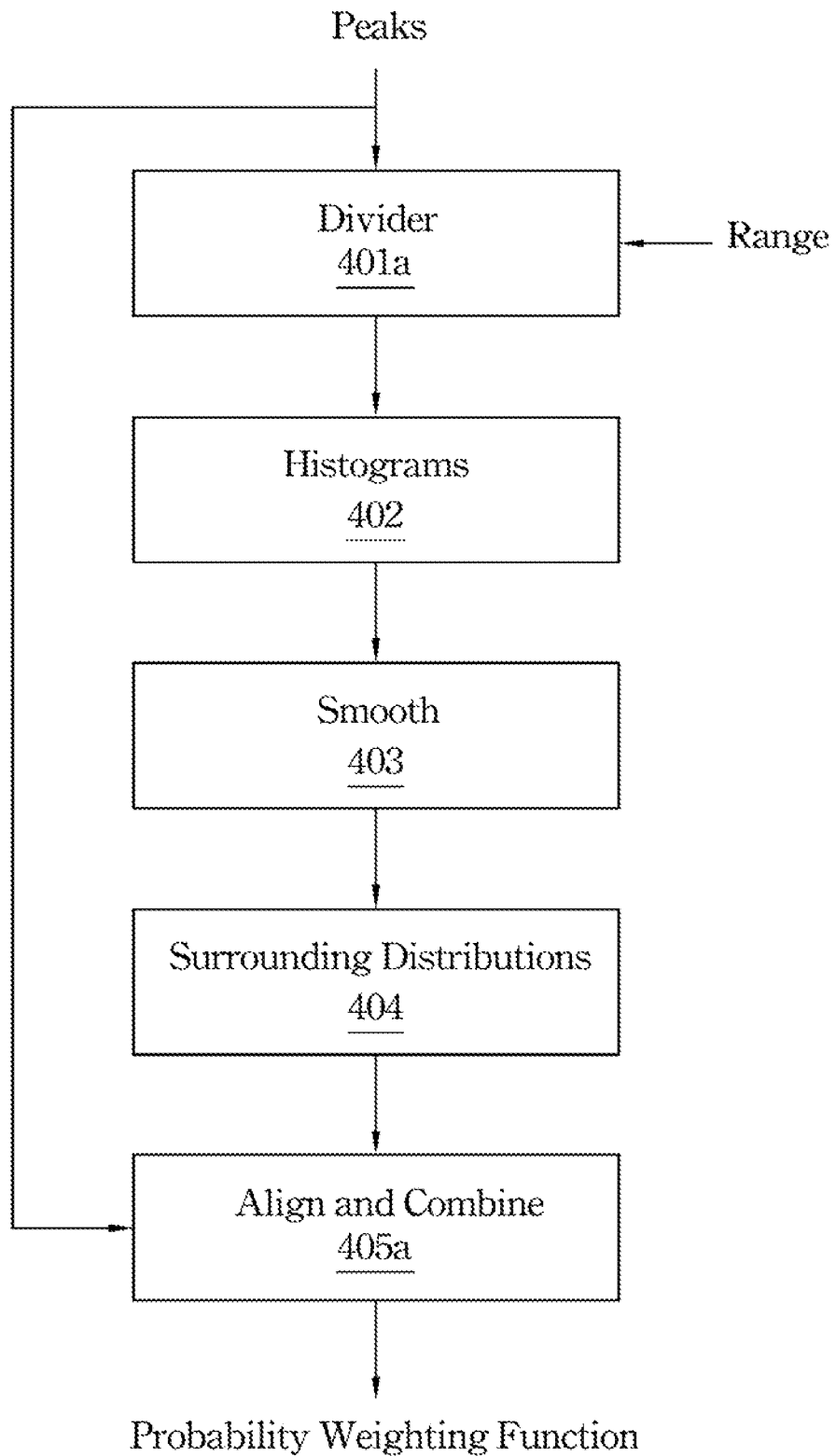
FIG. 4A, FIG. 4B, and FIG. 4C are a flowchart and illustrative diagrams for deriving the probability weighting function according to one embodiment of the present invention.
Figure 4B:
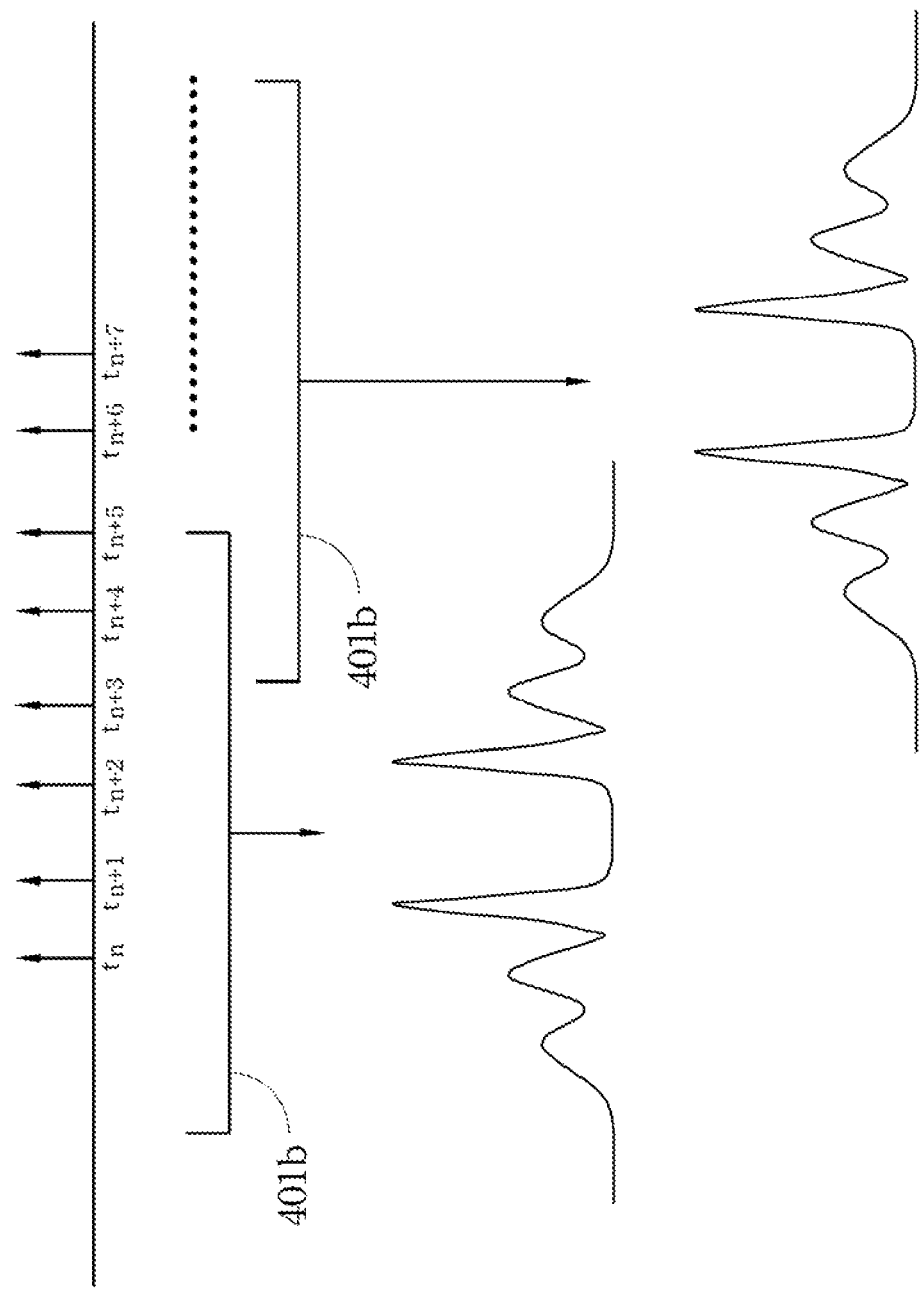
Figure 4C:
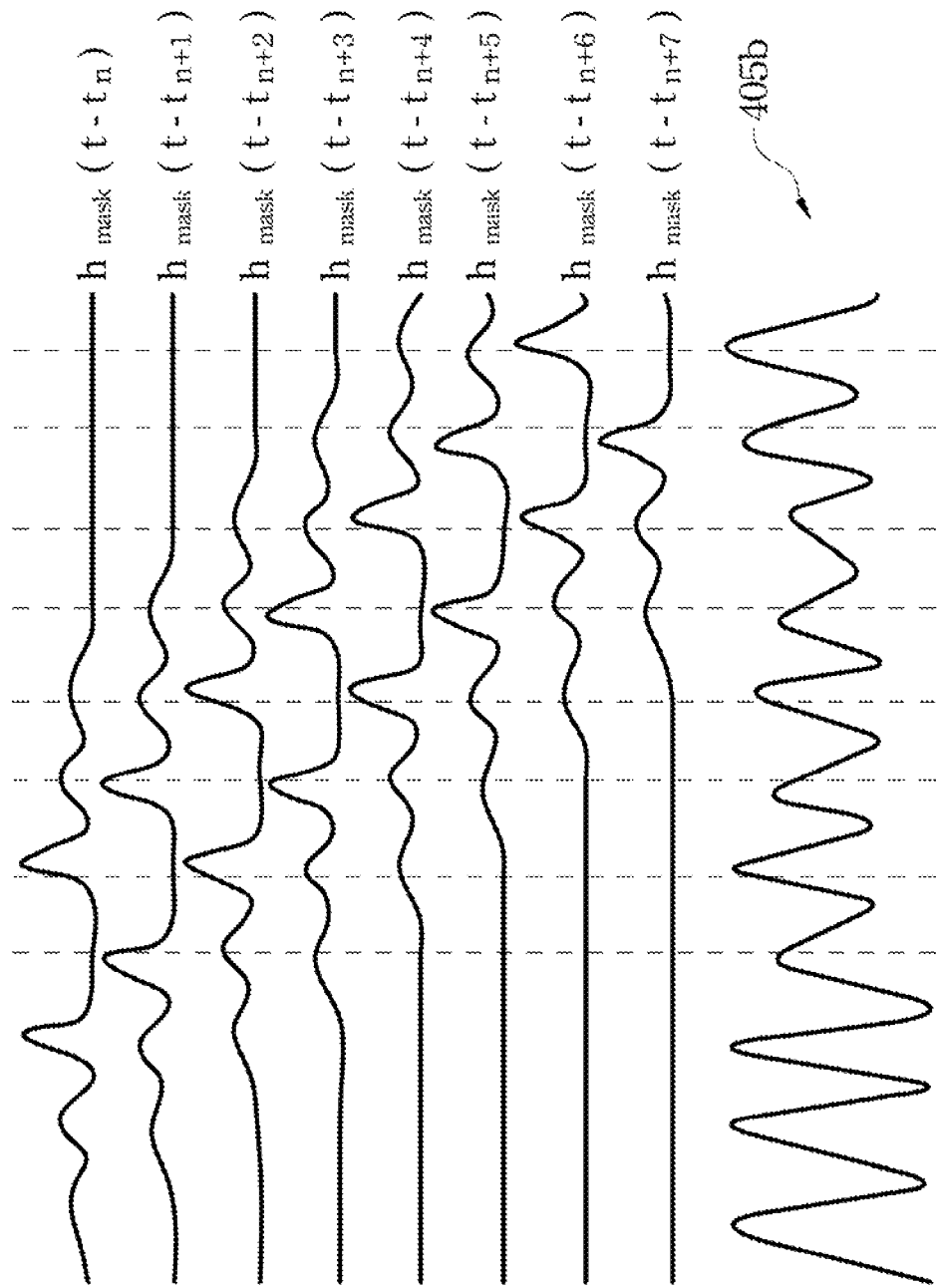

FIG. 4A, FIG. 4B, and FIG. 4C are a flowchart and illustrative diagrams for deriving the probability weighting function according to one embodiment of the present invention. The histograms are derived from different segments of identified peaks. The probability weighting function is derived first through defining ranges 401b (shown in FIG. 4B) for probability distribution estimation and dividing the identified peaks into segments according to the ranges in step 401a. Next, derive histograms of peak-to-peak intervals of each segment in step 402a and smooth the histogram when the range is small in step 403. After that, derives the surrounding distributions for each histogram in each segments in step 404a; and derive the probability weighting function by choosing the closest surrounding distribution and shifting the centers of them to each identified peak and adding all of them together in step 405a, and the probability weighting function 405b is thus derived.

Peak-to-Noise Ratio

Although the noise and interferences can be largely removed from abdominal composite ECG by using some kind of pre-processing method as previously mentioned, the decomposed fetus ECG signal may not necessarily larger than the noise that is not sufficiently removed. In this regard, a new parameter is created, peak-to-noise ratio (PNR), to compensate this weakness by quantifying the reliability of each peak.

Figure 5:
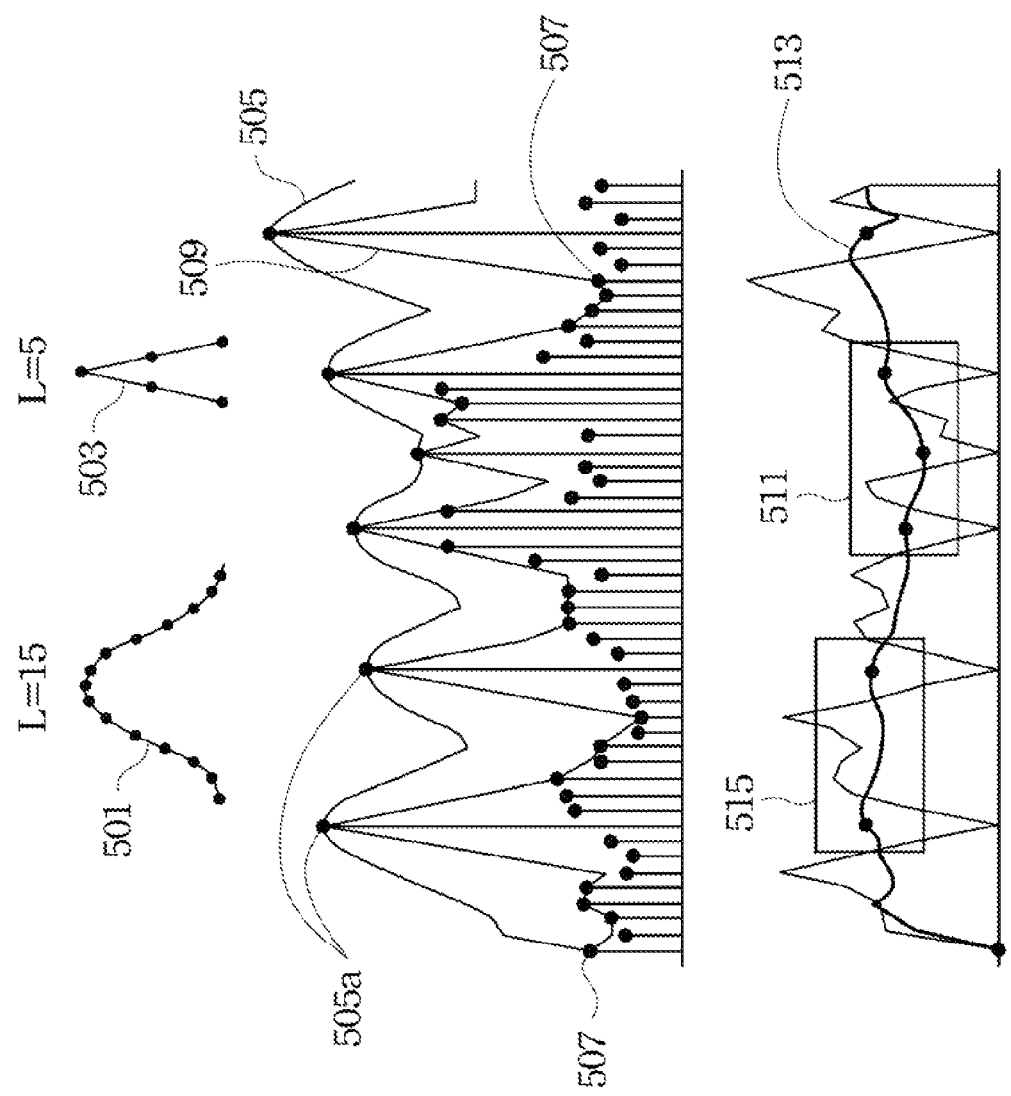
FIG. 5 shows the schematic diagram of PNR process according to one embodiment of the present disclosure.

After getting the fECG signals multiplied the weighting mask, the first step of the peak-to-noise ratio processes is to design two different lengths of sliding windows. The data points inside the windows are multiplied by two sizes of window functions to perform two different maximum-curves of the fECG signals, in which the larger maximum-curve is detected by larger window and vice versa. Each sliding window is the same as mentioned before has a maximum at a center and gradually decreased on both sides. In the following schematic diagram of maximum-curve processes, it is clearly to observe there exist an area between the two envelopes (curve 505 and curve 509 shown in FIG. 5) where also can be seen as the changes in the distance between the two maximum-curves. Next, according to each discrete signal as the center, the each mean of peak-to-noise ratio (PNR) is calculated by averaging the changes in the distance between the two fixed-length maximum-curves, that is the peak-to-noise ratio. It is believed that the greater PNR may present the higher probability of the correct peak and vice versa. FIG. 5 shows the schematic diagram of PNR process according to one embodiment of the present disclosure. The curve 501 indicates the larger fading window with 15 points-length, and the curve 503 indicates the smaller fading window with 5 points-length. The points 505a are the peaks detected by the larger fading window 501, and the points 507 are the peaks detected by the smaller fading window 503. The rectangular 515 is the calculated signal range of the high PNR, the rectangular 511 is the calculated signal range of the lower PNR, and the curve 513 is the variation of mean PNR value for each discrete signal.

PNR is to indicate the correctness of each peak. The greater PNR indicates there is fewer peak like noise around that peak, that is, the higher accuracy of the peak. It is helpful to eliminate the incorrect peaks and to return the original fetal cardiac rhythmic.

In addition, a plenty of histograms are derived from different segments of identified peak points, and the probability weighting function further is derived through the following procedure: defining a range for probability distribution estimation and dividing the identified peaks into segments according to the range; deriving histogram of peak-to-peak intervals of each segment and smoothing the histogram when the range is small; deriving the surrounding distribution for each histogram in each segments; and deriving the probability weighting function by choosing the closest surrounding distribution and shifting the centers of them to each identified peak and adding all of them together.

It will be apparent to those skilled in the art that various modifications and variations can be made to the structure of the present invention without departing from the scope or spirit of the invention. In view of the foregoing, it is intended that the present invention cover modifications and variations of this invention provided they fall within the scope of the following claims.

What is claimed is:

1. A method, implemented through an electronic system, for processing sequential data to identify a plurality of possible peak points relating to stochastic properties of historical results, comprising the steps of:
   (a) identifying the possible peak points of the sequential data;
   (b) deriving a probability weighting function from the identified peak points, wherein the step (b) comprises:
   deriving a distribution function through creating and normalizing a histogram of a plurality of peak-to-peak intervals;
   deriving an extended distribution function through adding a plurality of copies of the distribution function with different time ranges;
   deriving a surrounding probability distribution that surround search peak point through adding the extended distribution function and a mirror of the extended distribution function in the opposite direction; and
   duplicating a plurality of copies of the surrounding probability distribution, shifting the copies of the surrounding probability distribution and aiming the center of each copy at each identified peak of the sequential data, and adding a probability distribution of all the copies of the surrounding probability distribution together to form the probability weighting function;
   (c) deriving a weighted sequential data through weighting the sequential data by the probability weighting function; and
   (d) identifying possible peak points of the weighted sequential data, wherein the step (d) comprises:
   using a divider of an electrocardiogram measure machine for partitioning the sequential data into a plurality of segments by grouping each data point with surrounding data points into one of the segments:
   using a multiplier of the electrocardiogram measure machine for deriving a plurality of weighted segments through weighting the surrounding data points in each of the segments; and
   identifying the peak points, wherein each of the peak points is associated with a particular weighted segment, so that the electrocardiogram measure machine enhances peak signals of a fetal electrocardiogram.

2. The method of claim 1, further comprising:
   repeating the step (b) to the step (d).

3. The method of claim 1, wherein the sequential data is two dimensional data.

4. The method of claim 1, wherein a plurality of histograms are derived from different segments of identified peaks, and steps of deriving the probability weighting function further comprising:
   defining a range for probability distribution estimation and dividing the identified peaks into segments according to the range;
   deriving histogram of peak-to-peak intervals of each segment;
   deriving the surrounding distribution for each histogram in each segments; and
   deriving the probability weighting function by choosing the closest surrounding distribution and shifting the centers of them to each identified peak and adding all of them together.

* * * * *